United States Patent [19]

Amato et al.

[11] Patent Number: 5,380,838
[45] Date of Patent: Jan. 10, 1995

[54] STABLE SOLVATES OF AVERMECTIN COMPOUNDS

[75] Inventors: Joseph S. Amato, Brooklyn, N.Y.; Raymond Cvetovich, Scotch Plains, N.J.

[73] Assignee: Merck & Co. Inc., Rahway, N.J.

[21] Appl. No.: 133,494

[22] Filed: Oct. 8, 1993

[51] Int. Cl.$^6$ .................. A61K 31/71; C07D 407/14
[52] U.S. Cl. ..................... 536/7.1; 549/264
[58] Field of Search ........... 514/30; 536/7.1, 4, 536/9, 17; 549/264

[56] References Cited

U.S. PATENT DOCUMENTS

| | | | |
|---|---|---|---|
| 4,171,314 | 10/1979 | Chabala et al. | 549/264 |
| 4,199,569 | 4/1980 | Chabala et al. | 514/30 |
| 4,206,205 | 6/1980 | Mrozik et al. | 424/180 |
| 4,310,519 | 1/1982 | Albers-Schonberg et al. | 424/181 |
| 4,457,920 | 7/1984 | Mrozik | 424/180 |
| 4,657,854 | 4/1987 | Wegfahrt | 435/14 |
| 4,734,375 | 3/1988 | Charlton | 436/74 |
| 4,812,400 | 3/1989 | Steinman | 435/21 |

FOREIGN PATENT DOCUMENTS 0275398 7/1988 European Pat. Off. .

OTHER PUBLICATIONS

The Merck Index, Eleventh Edition, Abstract 1, p. 1; & Abstract 5133, pp. 825–826.
Outlaw W. H., Measurement of $10^{-7}$–$10^{-12}$ Mol of Potassium . . . Anal Biochem 92, 370–374 1979.
Sumiyoshi H., Single & Rapid Determination of K & Na, Chem Abstracts 90 (19):148113t 1977.
Wimmer M. C., A Kinetic Colorimetric Procedure for Quatifying Mg in Serum., Clin Chem 32/4 629–632 1986.

*Primary Examiner*—John W. Rollins
*Assistant Examiner*—Howard C. Lee
*Attorney, Agent, or Firm*—Sylvia A. Ayler; Mark R. Daniel; Joseph F. DiPrima

[57] ABSTRACT

There is disclosed a novel form of avermectin compounds wherein the avermectin compounds are crystallized as alcohol solvates to greatly enhance stability of the avermectin drug during long-term storage. The avermectin compounds have utility as highly potent antiparasitic, insecticidal, and anthelmintic agents and compositions for that use are also disclosed.

5 Claims, No Drawings

STABLE SOLVATES OF AVERMECTIN COMPOUNDS

BACKGROUND OF THE INVENTION

The term avermectin (previously referred to as C-076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519. The natural avermectin compounds are a series of macrolides, each of which is substituted therein at the 13-position with a 4-(α-L-oleandrosyl)-α-L-oleandrose group. The preparation and properties of synthetic avermectin aglycones in which the disaccharide moiety has been removed leaving a free hydroxyl group at position 13 have been described by Mrozik el al., *J. Org. Chem.* 1982, 47,489–492 and by Chabala et al., *J. Med. Chem.* 1980, 23, 1134–1136. Additionally, U.S. Pat. No. 4,199,569 reveals the 22,23-dihydro avermectin compounds. The avermectin compounds and the instant derivatives thereof have a very high degree of anthelmintic and anti-parasitic activity. The natural compounds have the following general structure:

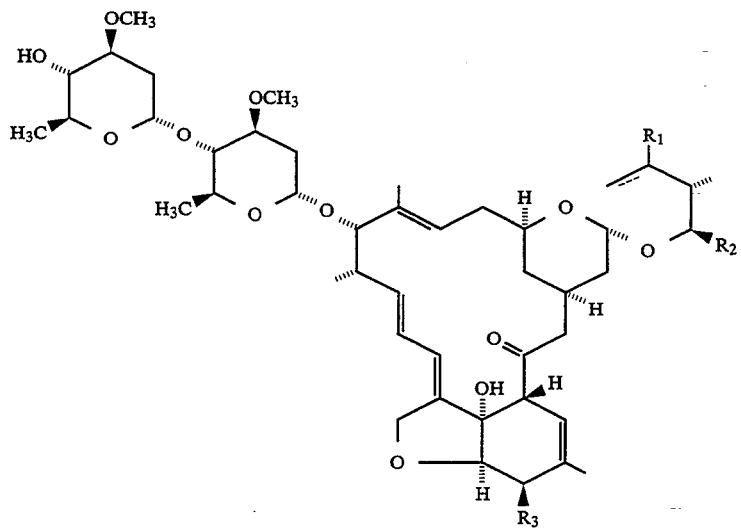

wherein the broken line at the 22,23-position indicates a single or double bond and;

R$_1$ is hydroxy and is present only when said broken line indicates a single bond;

R$_2$ is isopropyl or sec-butyl; and

R$_3$ is methoxy or hydroxy.

There are eight major natural avermectin compounds, designated A1a, A1b, A2a, A2b, B1a, B1b, B2a and B2b. These designations are based on the structure of the individual compounds as shown in the following table (referring to the foregoing structural formula).

| Compound | 22,23-bond | R$_1$ | R$_2$ | R$_3$ |
|---|---|---|---|---|
| A1a | double bond | — | sec-butyl | —OCH$_3$ |
| A1b | double bond | — | isopropyl | —OCH$_3$ |
| A2a | single bond | —OH | sec-butyl | —OCH$_3$ |
| A2b | single bond | —OH | isopropyl | —OCH$_3$ |
| B1a | double bond | — | sec-butyl | —OH |
| B1b | double bond | — | isopropyl | —OH |
| B2a | single bond | —OH | sec-butyl | —OH |
| B2b | single bond | —OH | isopropyl | —OH |

The avermectins are generally isolated as mixtures of the "a" and "b" components (typically ≧80% "a" and ≦20% "b"). Such compounds differ only in the nature of the R$_2$ substituent and this minor structural difference has been found to have very little effect on the chemical reactivity or hie, logical activity of the compounds. Thus, although the "a" and "b" components can be separated from each other by chromatography this is not necessary and hence is not normally done. The presence of a mixture of "a" and "b" components may be indicated by dropping the "a" or "b" from the designation of the compound. A mixture of avermectin B1a and avermectin B1b is thus referred to as avermectin B1. Alternatively, a slash(/) is inserted between the compound designations to indicate a mixture such as in "B1a/B1b".

The above structural formula is shown without a definitive stereochemistry at certain positions and with a defined stereochemistry at other positions. However, during the course of the synthetic procedures used to prepare such compounds, or using racemization or epimerization procedures known to those skilled in the art, the products of such procedures can be a mixture of stereoisomers. In particular, the stereoisomers at the 13- and 23-positions may be oriented either α- or β- representing such groups being below or above the general plane of the molecule, respectively. In each such case, and at other positions in the molecule, both the α- and β- configurations are intended to be included within the ambit of this invention.

A related family of natural products is known as the milbemycins. The milbemycins have the same macrocyclic ring structure as the avermectins but have no substitution at position 13 and have a methyl or ethyl group at position 25 (R$_2$=methyl or ethyl rather than isopropyl or sec-butyl as in the avermectins). The milbemycins and the fermentation conditions used to prepare them are described in U.S. Pat. No. 3,950,360. Closely related 13-deoxyavermectin aglycones are prepared by chemical modification of the natural avermectins and have been described in U.S. Pat. Nos. 4,171,134 and 4,173,571.

Stabilization of the avermectin class of compounds depends on the particular compound of interest and the method of stabilization. For example, some avermectin compounds require the addition of antioxidants such as propyl gallate, BHA (butylated hydroxy anisole), BHT (butylated hydroxy toluene), monothioglycerol, vitamin E and the like, to the bulk product to inhibit degradation. Other avermectins have been stabilized by the formation of benzoate salts. The present invention is different in that stabilization of avermectins is significantly increased by recrystallization of the product with a sterically encumbered alcohol which results in a new form of avermectin molecule whereby the spatial arrangement of the alcohol in the crystal leads to enhanced thermal stability.

SUMMARY OF THE INVENTION

The instant invention is concerned with a novel form of avermectin compounds wherein the avermectin compounds are recrystallized as alcohol solvates which provide a stable bulk product at ambient temperatures during long-term storage. Thus, it is an object of the present invention to describe such stable avermectin alcohol solvates. A further object is to describe processes for the preparation of such compounds. A still further object is to describe the uses of such compounds as anti-parasitic agents and anti-bacterial agents. Still further objects will become apparent from a reading of the following description.

DETAILED DESCRIPTION OF THE INVENTION

The compounds of the instant invention have the following structural formula:

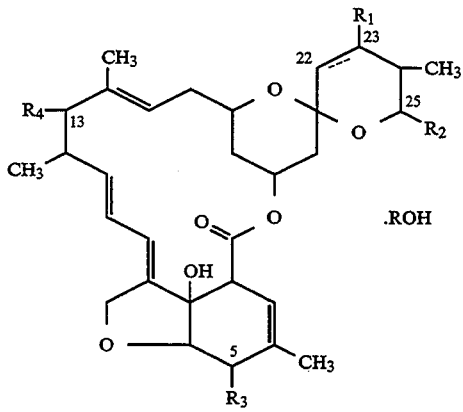

where the broken line indicates a single or a double bond at the 22,23-positions;

R is an alkyl group of from 3 to 4 carbon atoms resulting in an alcohol consisting of isobutanol, isopropanol, propanol or butanol;

$R_1$ is hydrogen or hydroxy, and is hydroxy only when the broken line indicates a single bond;

$R_2$ is an alkyl group of from 1 to 6 carbon atoms or alkenyl of from 3 to 6 carbon atoms or cycloalkyl of from 3 to 6 carbon atoms;

$R_3$ is hydroxy, methoxy, or $=NOR_5$;

$R_5$ is hydrogen or methyl; and $R_4$ is hydrogen, hydroxy, ($C_1$-$C_3$ alkoxy)(—$C_0$-$C_3$ alkoxy)methoxy, or

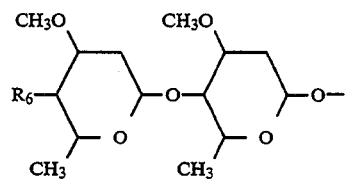

where $R_6$ is hydroxy, $C_1$-$C_3$ amino, or $C_2$-$C_3$ alkanoylamino.

The preferred avermectin compounds of the instant invention are the 22,23-dihydro-avermectins and the-13-polyalkoxy avermectin aglycones, most preferably 22,23-dihydro-13-0-[(2-methoxyethoxy)-methyl]avermectin-B1-aglycone (22,23-$H_2$-13-O-MEM IVM B1 aglycone).

The alcohols used in the instant invention are the $C_3$ thru $C_4$ alcohols such as isobutanol, isopropanol and the like, most preferably isopropanol.

PREPARATION OF STARTING MATERIALS

The starting materials for this invention are disclosed in Albers-Schonberg et al., J. Am. Chem. Soc. 1981, 103, 4216–4221 and references cited therein (naturally occurring avermectins), Chabala et al., J. Med. Chem. 1980, 23, 1134–1136 (22,23-dihydro avermectin B1 (Ivermectin), and 22,23-dihydro avermectin B1-aglycone, and U.S. Pat. No. 4,587,247.

The novel compounds of this invention are potent anthelmintic and anti-parasitic agents against internal and external parasitic infestations and are prepared as stable alcohol solvates by the following procedures:

The avermectin compound (1 part) is dissolved in isopropanol (1–20 parts) under nitrogen at temperatures ranging from 50° C. to 75° C., preferably from 60° C. to 70° C. and stirring the mixture thus formed at this temperature for 10 to 60 minutes. To the mixture thus generated is added water (0–20 parts). The intended volume of water can be added in part or whole and the amount added at this point is added at a rate such that a temperature above 50° C. is maintained. The resultant solution is then cooled to from about 30° C. to 40° C., preferably from about 35° C. to 40° C. over a period from about ½ hour to 1½ hours. The solution is then seeded with from about 0.005 grams to 0.1 grams of 22,23 dihydro avermectin aglycone or the isopropanol solvate thereof. After seeding, the mixture is cooled to from about 25° C. to 15° C., preferably 20° C., over a period of 3 to 20 hours and aged at this temperature from about 0 to 24 hours. To the cooled seeded solution, if the intended volume of water is added in part, is added the final part (volume) of water over a period of 15 to 30 minutes. The resulting slurry is then cooled to from about 0° to 5° C. and aged at from about 0° to 10° C. for approximately 0 to 6 hours. The crystals are then filtered and washed in a 1:1 isopropanol/water solution and dried at room temperature under inert conditions.

The instant compounds of this invention are unexpectedly potent antiparasitic agents against endo and ecto parasites, particularly helminths and arthropods, which cause numerous parasitic diseases in humans, animals and plants.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevelant and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonchus and Ostertagia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Infections by ectoparasitic arthropods such as ticks, mites, lice, stable flies, hornflies, blowflies, fleas, and the like are also a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasite at the same time since infection by one parasite may weaken the animal and make it more susceptible to infection by a second species of parasite. Thus, a compound with a broad spectrum of activity is particularly advantageous in the treatment of these diseases. The compounds of this invention have unexpectedly high activity against these parasites, and in addition are also active against Dirofilaria in dogs, Nematospiroides and Syphacia in rodents, biting insects, and migrating diperous larvae such as Hypoderma sp. in cattle, and Gastrophilus in horses.

The instant compounds are also useful against endo and ecto parasites which cause parasitic diseases in humans. Examples of such endoparasites which infect man include gastro-intestinal parasites of the genera Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra-intestinal stages of the intestinal worms Strongylides and Trichinella. Ectoparasites which parasitize man include arthropods such as ticks, fleas, mites, lice, and the like and, as with domestic animals, infections by these parasites can result in transmission of serious and even fatal diseases. The instant compounds are active against these endo and ecto parasites and in addition are also active against biting insects and other dipterous pests which annoy humans.

The instant compounds are also useful against common household pests such as Blatella sp. (cockroach), Tineola sp. (clothes moth), Attagenus sp. (carpet beetle), Musca domestica (housefly) and against Solenopsis Invicta (imported fire ant).

The compounds are furthermore useful against agricultural pests such as aphids (Acyrthiosiphon sp.), locusts, and boll weevils as well as against insect pests which attack stored grains such as Tribolium sp. and against immature stages of insects living on plant tissue. The compounds are also useful as a nematodicide for the control of soil nematodes which may be agriculturally important.

For use as an antiparasitic agent in animals the instant compounds may be administered internally either orally or by injection, or topically as a liquid drench or as a shampoo.

For oral administration, the compounds may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the instant compounds and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either by mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds may alternatively be administered parenterally via injection of a formulation consisting of the active ingredient dissolved in an inert liquid carder. Injection may be either intramuscular, intraruminal, intratracheal, or subcutaneous. The injectable formulation consists of the active ingredient mixed with an appropriate inert liquid carrier. Acceptable liquid carders include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carders. The formulations are prepared by dissolving or suspending the active ingredient in the liquid carrier such that the final formulation contains from 0.005 to 10% by weight of the active ingredient.

Topical application of the instant compounds is possible through the use of a liquid drench or a shampoo containing the instant compounds as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds.

The instant compounds are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the compounds of these invention may be used individually or in combination with each other or with other unrelated antiparasitic agents. The dosage of the instant compounds required for best results depends on several factors such as the species and size of the animal, the type and severity of the infections, the method of administration and the compound used. Oral administration of the instant compounds at a dose level of from 0.0005 to 10 mg per kg of animal body weight, either in a single dose or in several doses spaced a few days apart, generally gives good results. A single dose of one of the instant compounds normally gives excellent control however repeat closes may be given to combat re-infection or for parasite species which are unusually persistent. The techniques for administering these compounds to animals are known to those skilled in the veterinary field.

The compounds of these invention may also be used to combat agricultural pests which attack crops either in the field or in storage. The compounds are applied for such uses as sprays, dusts, emulsions and the like either to the growing plants or the harvested crops. The techniques for applying these compounds in this manner are known to those skilled in the agricultural arts.

The following example is provided in order that this invention might be more fully understood; it is not to be construed as limitative of the invention. The avermectin derivative prepared in the following example is characterized using; techniques such as High Performance Liquid Chromatography (HPLC), X-ray crystallography, and the like.

EXAMPLE 1

22,23-Dihydro-13-O-[(2-methoxyethoxy)methyl] Avermectin-B1-Aglycone (22,23-$H_2$-13-O-MEM AVM B1 aglycone) Isopropanol Solvate 50 grams of 22,23-$H_2$-13-O-MEM AVM B1 aglycone was dissolved in 500 ml of isopropanol under a $N_2$ stream. The slurry was heated to 65° C. to obtain a clear yellow solution. To this solution was added 350 ml of water at a rate to keep the temperature of the solution above 50° C. The solution was allowed to cool to 39° C. and then seeded with 50 milligrams of 22,23-$H_2$-13-O-MEM AVM B1 aglycone isopropanol solvate. The seeded solution was then cooled from 39° C. to 30° C. at a rate of 3° C. per half hour and from 30° C. to 21° C. at a rate of 1° C. per hour. The cooled seeded solution was then contacted with the final volume of water (150 mls) which was added over a 20 minute period and resulted in a slurry of 22,23-$H_2$-13-O-MEM AVM B1 aglycone crystals. The slurry was cooled to 0°±5° C. and aged at 0°±10° C. for three hours. The crystals were filtered and washed with 2×50 mls of isopropanol/$H_2O$ (1:1) and dried using a nitrogen stream to yield 58.5 grams of stable 22,23-$H_2$-13-O-MEM AVM B1 aglycone isopropanol solvate. The HPLC area % and weight % were 97.3% and 97%, respectively.

EXAMPLE 2

13-O-MEM AVM B1 aglycone Isopropanol Solvate 25 grams of 13-O-MEM AVM B1 aglycone was added to 300 ml of isopropanol and heated to 65° C. under nitrogen to obtain a clear solution. Water (200 ml) was added keeping the temperature above 50° C. The solution was cooled to 39° C. over 30 minutes then seeded with crystalline 13-O-MEM AVM B1 aglycone isopropanol solvate (5 mg). The temperature of the mixture was cooled to 20° C. over 3 hours and aged at 20° C. for 14 hours and the slurry was cooled to 5° C. and aged at 5° C. for 3 hours. The crystals were filtered and displacement washed twice with 1:1 isopropanol/water (25 ml). The product dried with the passage of nitrogen through the cake at 25° C.

The structure of the 13-O-MEM AVM B1 aglycone isopropanol solvate of the present invention is shown below:

wherein $R_2$ is $CH_3$, or $CH_2CH_3$.

The compound crystallizes as an isopropanol solvate in a crystallographic space group $P2_12_12_1$. These compounds show significant long term stability when stored at temperatures ranging from about −10° C. to 30° C., preferably from about −5° C. to 20° C.

EXAMPLE 3

Stability Results 22,23-$H_2$-13-O-MEM AVM B1 aglycone Isopropyl solvate and ethanol solvate, were HPLC assayed before being stored under room temperature (25° C.), and accelerated (40° C.) conditions (ambient relative humidity) in sealed containers for 28 weeks. The samples were then HPLC assayed for purity after storage. The ethanol solvate exhibited 9% decomposition after 28 weeks at room temperature, while the more preferred isopropanol solvate did not decompose. See Table 1 below.

TABLE 1

| Storage Conditions | Solvate | Initial | 28-weeks | % decomposition |
|---|---|---|---|---|
| room temp. | EtOH | 92.5 | 80.6 | 12 |
| " | i-PrOH | 94.9 | 95.6 | 0 |
| 40° C. | i-PrOH | 94.9 | 91.4 | 4 |

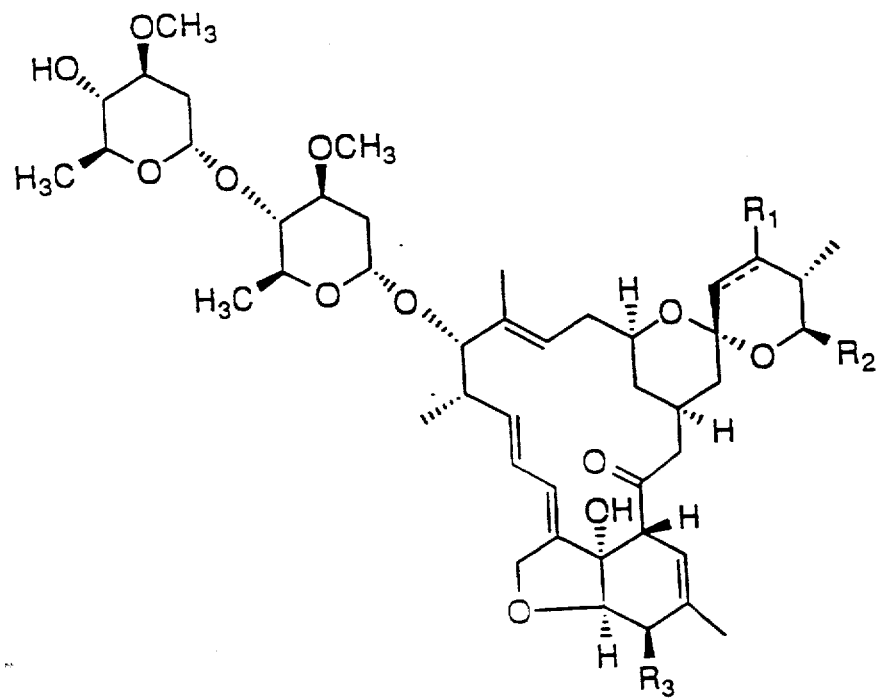

What is claimed is:

1. An avermectin alcohol solvate compound having the formula:

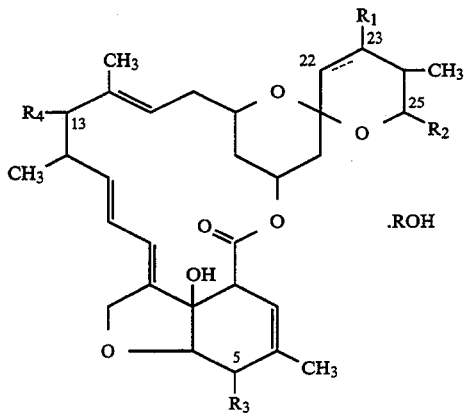

where the broken line indicates a single or a double bond at the 22,23-positions;

R is an alkyl group of 3 carbon atoms resulting in an alcohol consisting of isopropanol;

$R_1$ is hydrogen or a hydroxy and is hydroxy only when the broken line indicates a single bond;

$R_2$ is an alkyl group of from 1 to 6 carbon atoms or an alkenyl group of from 3 to 6 carbon atoms or cycloalkyl group of from 3 to 6 carbon atoms;

$R_3$ is hydroxy, methoxy or $=NOR_5$;

$R_5$ is hydrogen or methyl; and $R_4$ is hydrogen, hydroxy, ($C_1$–$C_3$ alkoxy)(—$C_0$–$C_3$ alkoxy)methoxy or

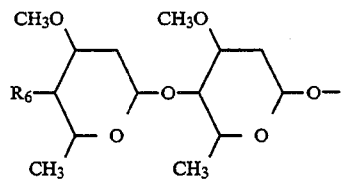

where $R_6$ is hydroxy, $C_1$–$C_3$ amino or $C_2$–$C_3$ alkanoylamino.

2. The compound of claim 1 wherein $R_4$ is (C1 alkoxy)(C2 alkoxy)methoxy.

3. A 22,23,dihydro-13-O-[(2-methoxyethoxy)-methyl]avermectin B1 aglycone isopropanol solvate wherein the crystallographic environment is $P2_12_12_1$.

4. A 22,23-dihydro-13-O-[(2-methoxyethoxy)-methyl]avermectin B1 aglycone isopropanol solvate compound having the formula:

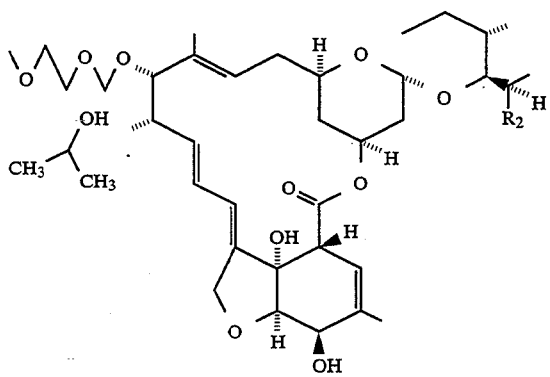

wherein $R_2$ is $CH_3$, or $CH_2CH_3$.

5. A composition useful for treating animals infected with internal and external parasites which comprises an inert ingredient and alcohol solvates of claim 1.

* * * * *

UNITED STATES PATENT AND TRADEMARK OFFICE
CERTIFICATE OF CORRECTION

PATENT NO. : 5,380,838
DATED : January 10, 1995
INVENTOR(S) : Joseph S. Amato, et al.

It is certified that error appears in the above-indentified patent and that said Letters Patent is hereby corrected as shown below:

Column 1, lines 25-49, formula should read as shown on the attached page:

Signed and Sealed this

Twentieth Day of June, 1995

Attest:

BRUCE LEHMAN

*Attesting Officer*     *Commissioner of Patents and Trademarks*